United States Patent [19]

Sangekar et al.

[11] Patent Number: 4,992,277
[45] Date of Patent: Feb. 12, 1991

[54] IMMEDIATE RELEASE DILTIAZEM FORMULATION

[75] Inventors: Surendra Sangekar, Union; Winston A. Vadino, Whitehouse Station, both of N.J.; Eugenio A. Cefali, Plantation, Fla.

[73] Assignee: Schering Corporation, Kenilworth, N.J.

[21] Appl. No.: 399,050

[22] Filed: Aug. 25, 1989

[51] Int. Cl.$^5$ ................................................ A61K 9/20
[52] U.S. Cl. .................................... 424/465; 424/468; 424/469; 424/488; 424/499; 424/501
[58] Field of Search ............... 424/501, 499, 464, 465, 424/468, 469, 470, 488

[56] References Cited

U.S. PATENT DOCUMENTS

| | | | |
|---|---|---|---|
| 4,389,393 | 6/1983 | Schor et al. | 424/19 |
| 4,411,933 | 10/1983 | Samejima et al. | 427/213 |
| 4,443,497 | 4/1984 | Samejima et al. | 427/213 |
| 4,462,982 | 7/1984 | Samejima et al. | 424/35 |
| 4,542,042 | 9/1985 | Samejima et al. | 427/213 |
| 4,721,619 | 1/1988 | Panoz et al. | 424/459 |
| 4,784,858 | 11/1988 | Ventouras | 424/469 |
| 4,814,181 | 3/1989 | Jordan et al. | 424/473 |

FOREIGN PATENT DOCUMENTS

| | | |
|---|---|---|
| 898819 | 5/1984 | Belgium . |
| 900817 | 2/1985 | Belgium . |
| 900824 | 2/1985 | Belgium . |
| 901359 | 4/1985 | Belgium . |
| 903540 | 2/1986 | Belgium . |
| 315197 | 5/1989 | European Pat. Off. . |
| 59-010512 | 1/1984 | Japan . |
| 59-059632 | 4/1984 | Japan . |
| 59-065009 | 4/1984 | Japan . |
| 61-212517 | 9/1986 | Japan . |
| 62-005915 | 1/1987 | Japan . |

Primary Examiner—Thurman K. Page
Attorney, Agent, or Firm—Anita W. Magatti; James R. Nelson; Stephen I. Miller

[57] ABSTRACT

An immediate release diltiazem tablet is disclosed that exhibits an unexpectedly rapid bioavailability profile when the active ingredient is diltiazem.

3 Claims, No Drawings

IMMEDIATE RELEASE DILTIAZEM FORMULATION

SUMMARY

The present invention encompasses immediate release oral dosage forms and formulations for diltiazem.

One such oral dosage form is a tablet comprising an effective amount of diltiazem and excipients which may be compressed into a suitable oral dosage form, and which may be coated with one or more coating agents.

In a particular formulation described herein, an immediate release tablet may contain diltiazem or a pharmaceutically acceptable salt thereof in combination with swellable hydrophilic polymers and other auxiliary excipients such as sugar, magnesium stearate and/or povidone.

BACKGROUND OF THE INVENTION

Numerous references disclose diltiazem in sustained release formulations which utilize microencapsulation technology. For example are the following:

U.S. Pat. No. 4,452,042, issued to Samejima et al. on Sept. 17, 1985;

U.S. Pat. No. 4,462,982, issued to Samejima et al. on July 31, 1984;

U.S. Pat. No. 4,443,497, issued to Samejima et al. on Apr. 17, 1984; and

U.S. Pat. No. 4,411,933, issued to Samejima et al. on Oct. 25, 1983.

Similarly, numerous publications have disclosed devices which rely upon an osmotically regulated membrane for the controlled delivery of pharmaceuticals, such as diltiazem. For example, are the following:

Belgian Application No. 900817, published on Feb. 1, 1985 discloses a device comprising a semipermeable wall, an osmopolymer, such as poly(ethyleneoxide) and an active ingredient.

Belgian Application No. 900,824 also published on Feb. 1, 1985 discloses a core and a membrane having variable permeability.

Belgian Application No. 898,819, published on May 30, 1984, discloses a device for controlled drug delivery containing two compositions, including poly(ethyleneoxide).

Belgian Application No. 903,540 published Feb. 17, 1986 discloses a sustained release powder, which can be formulated into an ointment, suspension etc.

Belgian Application No. 901,359 published Apr. 16, 1985 discloses a controlled release diltiazem formulation containing granules and a semipermeable external membrane.

Japanese Application No. 175,144 published on Apr. 13, 1984, discloses a sustained release thermoset or thermoplastic resin.

Japanese Application No. 170,440 published on Apr. 5, 1984, discloses a sustained release tablet which utilizes hardened oil.

Japanese Kokai No. 62/5915, published Jan. 12, 1987, discloses diltiazem in combination with an acrylic acid resin.

Japanese Kokai No. 61/212517, published Sept. 20, 1986 discloses the use of diltiazem in combination with hydrogenated oils.

Japanese Kokai No. 59/10512 published Jan. 20, 1984, discloses microencapsulation of diltiazem, which is coated with ethylcellulose.

Panoz and Geohagan, U.S. Pat. No. 4,721,619 disclose an alternating arrangement (between 50 and 200 layers) of diltiazem, organic acid and lubricant layers and polymeric material layers built upon a central inert core.

Schor et al., U.S. Pat. No. 4,389,393 discloses a sustained release tablet which is one or more hydroxypropylmethyl celluloses of a mixture of one or more hydroxypropylmethyl celluloses and up to 30% by weight of the mixture of methylcellulose, sodium carboxymethyl cellulose and/or other cellulose ether, and wherein at least one of the hydroxypropylmethyl celluloses has a methoxy content of 16–24 weight percent, a hydroxypropyl content of 4–32 weight percent and a number average molecular weight of at least 50,000 and wherein the carrier base material constitutes less than about one third of the weight of the solid unit dosage form. Schor et al. do not include calcium channel blockers and in particular diltiazem as possible active ingredients (see column 4, lines 29 to 65).

However, none of the references disclose a diltiazem tablet formulation utilizing a uniformly dispersed hydrophilic matrix which gives an immediate release preparation.

DETAILED DESCRIPTION

The present invention relates to a novel immediate release tablet, useful in that it exhibits unexpectedly rapid in vivo activity over a short period of time. This is surprising because the tablet shows sustained release in vitro and contains a hydrophilic matrix in an amount that has usually given a sustained release profile; one would expect in vitro results to be predictive of in vivo results. Despite a prolonged in vitro dissolution profile due to the presence of a swellable hydrophilic polymer (hydroxypropylmethyl cellulose), the tablets of this invention were surprisingly found to have equivalent bioavailability in humans as compared to a commercially available immediate release diltiazem hydrochloride tablet from Marion Labs (Cardizem). The immediate release diltiazem tablets described herein therefore may be suitable for multiple daily administrations, or on an event triggered basis such as pectoral angina.

A preferred immediate release tablet falling within the scope of the invention utilizes diltiazem or a solvate thereof as the active ingredient. Preferably the amount of the active ingredient, such as diltiazem hydrochloride, will be present at about 20 to 500 mg per tablet (3 to 80 percent by weight) more preferably at about 30 to 360 mg per tablet (3 to 57 percent by weight) and most preferably at about 90 to 240 mg per tablet (14 to 38 percent by weight).

The diltiazem utilized herein also encompasses other pharmaceutically acceptable acid addition salt forms thereof, as well as other pharmaceutically acceptable salts and esters thereof, e.g., diltiazem tatarate. As described above, the diltiazem used in Example 1 below is the hydrochloride salt. Also included herein are stereospecific salt forms of diltiazem, both in pure form and racemic mixture. One such example is the (d,1) lactate form of diltiazem.

The tablets of the invention utilize a swellable hydrophilic polymer, into which the active ingredient is incorporated. The tablets also include other auxiliary excipients. These dosage forms slowly hydrate as they come in contact with gastric fluid or aqueous media and release the active ingredient by diffusion and/or erosion of the swollen matrix layer.

Examples of swellable hydrophilic polymers include: hydroxypropylmethyl cellulose; hydroxypropyl cellulose; methyl cellulose; hydroxymethyl cellulose; and hydroxyethyl cellulose, which can be used alone or in combination; carboxymethyl cellulose and the sodium salt thereof, which can be used alone or in combination; and other hydrocolloids, such as acacia and guar gum. The preferred swellable hydrophilic polymer is either hydroxypropylmethyl cellulose or hydroxypropyl cellulose.

The swellable hydrophilic polymers comprise from about 10 to about 30 percent by weight of the tablet. Preferably, the swellable hydrophilic polymers comprise from about 15 to about 25 percent by weight of the tablet and most preferably they comprise about 20 percent by weight of the tablet.

The hydroxypropylmethyl celluloses (HPMC) utilized in the present invention are water soluble cellulose ethers, and include, but not limited to, USP 2208, USP 2906 and USP 2910. Examples of such materials are commercially available from Dow Chemical Co. in various grades under several tradenames, including METHOCEL E, (USP 2910), METHOCEL F (USP 2906) and METHOCEL K (USP 2208). The various grades differ in methoxy and hydroxypropoxyl content as well as molecular weight and viscosity. Preferred hydroxypropylmethyl cellulose polymers useful in carrying out the invention include METHOCEL E4M, characterized by having a 28–30 weight percent methoxyl content, a 7–12 weight percent hydroxypropoxyl content, a number average molecular weight of 93,000 and a viscosity in a 2% aqueous solution of 3500–5600 cps (centipoises per second); and METHOCEL K100 having a 19–24 weight percent methoxyl content, a 7–12 weight percent hydroxypropoxyl content, a number average molecular weight of 24,6000, and a viscosity in a 2% aqueous solution of 100,000 cps; and METHOCEL F4M having a 26–30 weight (number average molecular weights of 85000–115000) percent methoxy content, a 4–6 weight percent hydroxypropoxyl content, a number average molecular weight of 86,000, and a viscosity in a 2% aqueous solution of 3500–5600 cps.

The hydroxypropyl cellulose utilized in the present invention is a high viscosity nonionic water soluble cellulose ether. These are commercially available, e.g. Klucel HXF manufactured by Aqualon Company, which is a member of the Aqualon Group of Wilmington, Del., is a fine particle size hydroxypropyl cellulose with a viscosity of a 1 percent aqueous solution of 1,500 to 3,000 cps.

Examples of auxiliary excipients utilized in the present invention include: diluents, binders and lubricants. The diluent may constitute from about 10 to about 50 percent by weight of the tablet but will preferably constitute from about 14 to about 38 percent by weight of the tablet. The diluent can be a sugar, e.g., mannitol or lactose, and lactose is preferred. Such lactose can be used in the direct tabletting grade as available from Shefield Corp. of Norwich, N.Y., and alternatively it can be used in the hydrous form or as spray dried lactose.

The binder used in the present invention comprises a polymeric binder that combines with the swellable hydrophilic polymer, and therefore includes low viscosity hydroxypropylmethyl cellulose, low viscosity hydroxypropyl cellulose, carboxymethyl cellulose and ethyl cellulose, as described above. The preferred binder is polyvinylpyrrolidone (povidone). The binder comprises from about 2 to about 6 percent by weight of the tablet, preferably about 4 percent by weight of the tablet.

The polyvinylpyrrolidone utilized in the present invention is a synthetic polymer consisting of linear 1-vinyl-2-pyrrolidinone groups in which the degree of polymerization results in polymers of various molecular weights. It is characterized by its viscosity in aqueous solution, relative to that of water, expressed as a K-value, ranging from 10 to 95. An example of a polyvinylpyrrolidone useful in the formulation of this invention is Povidone USP K29/32 having an average molecular weight of about 40,000 supplied by GAF Corp. Wayne, N.J.

Examples of lubricants utilized in the present invention include magnesium stearate, calcium stearate, stearic acid and the like, with the preferred lubricant being magnesium stearate. The lubricant comprises from about 0.5 to about 3 percent by weight of the tablet, preferably about 1 to about 3 percent by weight and most preferably about 1.5 percent by weight of the tablet. The lubricants are commercially available, e.g. magnesium stearate NF is commercially available from Mallinckrodt Inc., St. Louis, Miss.

In preparing the tablets of the invention, conventional tabletting techniques are employed, for example dry granulation or wet granulation, and direct compression. One method for manufacturing the tablets involves blending the diltiazem hydrochloride, the diluents and the hydrophilic binder, then granulating the mixture with a solution of the binder in water or alcohol or the mixture thereof. The granules can then be dried and milled if necessary. Any other ingredients such as lubricants (e.g., magnesium stearate) and the like are added to the granules and mixed. These granules are then dried, reduced to a suitable size and compressed into a suitable size and shape using conventional tabletting machines such as a rotary tablet press. These tablets may then be used as is or they can be film or sugar coated by techniques well known in the art.

The following examples describe typical tablet formulations, dissolution profiles, and bioavailability studies of the immediate release dosage forms of the present invention, but they are not to be interpreted as limiting the scope of the appended claims in any way.

EXAMPLE

Tablet Formulation, in vitro Dissolution and in vivo Bioavailability

Preparation of the tablet is as follows.

The mixture of diltiazem hydrochloride, lactose and hydroxypropylmethyl cellulose is granulated with a solution of povidone in water. The granules are then dried, reduced to suitable size and compressed into a suitable size and shape tablets after the addition of magnesium stearate. The tablets may be film or sugar coated.

| TABLET FORMULATION | |
|---|---|
| Composition | Amount (mg/tablet) |
| Diltiazem HCl | 90 |
| Lactose NF | 255 |
| Hydroxypropylmethyl cellulose | 100 |
| Povidone USP K29/32 | 25 |
| Magnesium stearate NF | 10 |

| TABLET FORMULATION | |
|---|---|
| Composition | Amount (mg/tablet) |
| | 480 mg |

Release rates were determined using the USP paddle method (as described in USPxxi) at 100 revolutions per minute in 1000 ml of purified water.

| IN VITRO TABLET DISSOLUTION | |
|---|---|
| Time (hrs.) | Percent Dissolved |
| 1 | 32 |
| 2 | 47 |
| 4 | 70 |
| 6 | 86 |
| 8 | 98 |

The tablets in the above example were tested in 6 normal volunteers in a cross over study using 90 mg immediate release tablet as a control (Cardizem, Marion Labs). The comparison of the following biopharmaceutical parameters demonstrates bioequivalency between the two tablets.

| | Mean $C_{max}$ (ng/ml) | $t_{max}$ (hours) | Mean AUC (ng/ml × hr) |
|---|---|---|---|
| Cardizem 90 mg | 147.3 | 3.4 | 881 |
| Tablet of Example above | 147.8 | 3.3 | 880.32 |

We claim:
1. An immediate release diltiazem tablet comprising:
   (a) 3 to 80 percent diltiazem hydrochloride;
   (b) 10 to 30 percent hydroxypropylmethyl cellulose;
   (c) 2 to 6 percent polyvinylpyrrolidone;
   (d) 0.5 to 3 percent magnesium stearate; and
   (e) 10 to 50 percent lactose.
2. The immediate release diltiazem tablet defined in claim 1 further comprising:
   (a) 3 to 57 percent diltiazem hydrochloride;
   (b) 15 to 25 percent hydroxypropylmethyl cellulose;
   (c) 2 to 6 percent polyvinylpyrrolidone;
   (d) 1 to 3 percent magnesium stearate; and
   (e) 14 to 38 percent lactose.
3. The immediate release diltiazem tablet defined in claim 2 further comprising:
   (a) 14 to 38 percent diltiazem hydrochloride;
   (b) 15 to 25 percent hydroxypropylmethyl cellulose;
   (c) about 4 percent polyvinylpyrrolidone;
   (d) 1 to 2 percent magnesium stearate; and
   (e) 14 to 38 percent lactose.

* * * * *